United States Patent [19]

Kawaki et al.

[11] Patent Number: 5,310,944
[45] Date of Patent: May 10, 1994

[54] PROCESS FOR PRODUCING CARBOXYLATED COMPOUND

[75] Inventors: Takao Kawaki, Tokyo; Yuh Miyauchi, Tsukuba; Toshio Watanabe, Tsukuba; Katsushige Hayashi, Tsukuba; Satoshi Ueno, Yamakita; Hiroshi Ogawa; Fumiya Zaima, both of Tsukuba, all of Japan

[73] Assignee: Mitsubishi Gas Chemical Company, Inc., Tokyo, Japan

[21] Appl. No.: 975,444

[22] Filed: Jan. 17, 1992

[30] Foreign Application Priority Data

Jan. 21, 1991 [JP] Japan .................................. 3-020505
Mar. 6, 1991 [JP] Japan .................................. 3-065690
Mar. 15, 1991 [JP] Japan .................................. 3-074353

[51] Int. Cl.$^5$ ................ C07D 313/04; C07D 309/30; C07D 307/33
[52] U.S. Cl. ................................. 549/266; 549/273; 549/295
[58] Field of Search ..................... 549/266, 273, 295

[56] References Cited

U.S. PATENT DOCUMENTS 3,993,673 11/1976 McMullen .................... 260/348.5 L

OTHER PUBLICATIONS

Journal of the American Chemical Society, vol. 101, No. 23, Nov. 7, 1979, pp. 6938-6946, S.E. Jacobson et al., "Biphase and Triphase Catalysis. Arsonated Polystyrenes as Catalysts in the Baeyer-Villiger Oxidation of Ketones by Aqueous Hydrogen Peroxide".

Chemical Abstracts, vol. 71, No. 13, Sep. 29, 1969, Abstract No. 60755A, p. 380.

Primary Examiner—C. Warren Ivy
Assistant Examiner—Ba K. Trinh
Attorney, Agent, or Firm—Wenderoth, Lind & Ponack

[57] ABSTRACT

A process for producing a carboxylated compound, which comprises reacting a carbonyl compound with hydrogen peroxide in the presence of an organo-arsenic acid of the formula (1),

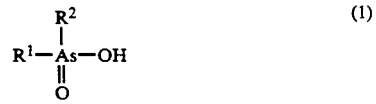

wherein:
$R^1$ is a $C_1$-$C_{12}$ alkyl group which may be substituted or an aryl group which may be substituted,
$R^2$ is a hydroxyl group or the same group as that which defines $R^1$,
or alternatively, $R^1$ and $R^2$ may bond to each other to form a five-membered or six-membered ring together with As atoms to which these groups are bonded, and
the substituent(s) substituted on the above groups is/are selected from hydroxyl, carboxyl, carbonyl, sulfonyl, sulfonium, an amino group, an ammonium group, an alkyl group, an alkoxyl group and a halogen atom,
while a water concentration in a reaction system is maintained at not more than 2% by weight, thereby to form a corresponding carboxylated compound.

12 Claims, No Drawings

PROCESS FOR PRODUCING CARBOXYLATED COMPOUND

DETAILED DESCRIPTION OF THE INVENTION

The present invention relates to a process for producing a carboxylated compound. More specifically, it relates to a process for producing a carboxylated compound which comprises reacting a carbonyl compound with hydrogen peroxide in the presence of an organo-arsenic acid.

Conventionally, Japanese Patent Publication No. 10243/1969 discloses a process for producing an ester in which a ketone and hydrogen peroxide are allowed to react in the presence of arsenic or an arsenic compound as a catalyst. This Patent Publication describes arsenic oxide, arsenic sulfide, arsenic selenide, arsenic halide, arsenate, arsenite, arsanilic acid, methyl arsine and salvarsan as arsenic compounds. The process using such a catalyst involves a formation of by-products in large quantity, and the intended product is obtained only at low yields if no reaction solvent is used.

Japanese Laid-open Patent Application No. 21481/1980 discloses a process in which the oxidation is carried out with hydrogen peroxide in the presence, as a catalyst, of a particulate or beads-like porous polymer in which an arsenic group is pendent from a polyphenylene or a polymethylene skeleton crosslinked with divinyl arylene.

In the process disclosed in the above Laid-open Patent Application, by-products are formed in large quantity unless a high concentration of hydrogen peroxide is used. Further, due to the use of a resin as a carrier, the reaction cannot be carried out at a relatively high temperature, and the reaction rate and the yield are low.

Japanese Patent Publication No. 35814/1989 discloses a process for producing a carboxylated compound comprising reacting a cyclic ketone or an aldehyde with hydrogen peroxide in the presence of at least one Friedel-Crafts catalyst such as HF, SbF$_5$ or SnCl$_4$, in which process water is continuously removed from the liquid reaction mixture by evaporation so that the reaction mixture is kept at a substantially anhydrous state. In the process disclosed in this Patent Publication, the reaction rate is high. However, the industrially crucial defects with this process are that it is required to use a high concentration of hydrogen peroxide in order to give high yields and that, although the system is kept in a substantially anhydrous state, it is required to use an expensive, corrosion-resistant reactor due to the use of corrosive hydrogen fluoride and due to the use of a catalyst which forms hydrogen fluoride and hydrogen chloride by hydrolysis.

It is an object of the present invention to provide a process for producing a carboxylated compound.

It is another object of the present invention to provide a process for producing a carboxylated compound from a carbonyl compound and hydrogen peroxide at high yields and at a high reaction rate.

It is further another object of the present invention to provide a process for industrially advantageously producing a carboxylated compound in the presence of a stable organo-arsenic acid which has high oxidation resistance and which can be separated from the reaction system after the reaction and recycled.

The other objects and advantages of the present invention will be apparent from the following description.

According to the present invention, the above objects and advantages of the present invention are achieved by a process for producing a carboxylated compound, which comprises reacting a carbonyl compound with hydrogen peroxide in the presence of an organo-arsenic acid of the formula (1),

wherein:
R$^1$ is a C$_1$-C$_{12}$ alkyl group which may be substituted or an aryl group which may be substituted,
R$^2$ is a hydroxyl group or the same group as that which defines R$^1$,
or alternatively, R$^1$ and R$^2$ may bond to each other to form a five-membered or six-membered ring together with As atoms to which these groups are bonded, and
the substituent(s) substituted on the above groups is/are selected from hydroxyl, carboxyl, carbonyl, sulfonyl, sulfonium, an amino group, an ammonium group, an alkyl group, an alkoxyl group and a halogen atom,
while a water concentration in a reaction system is maintained at not more than 2% by weight, thereby to form a corresponding carboxylated compound.

The organo-arsenic acid used in the present invention has the above formula (1). The above organo-arsenic acid has characteristic features in that it has high oxidation resistance, that after the reaction it can be separated by distillation or extraction with water or other solvent to recycle it to the reaction system, and that it has very high stability.

In the above formula (1), R$^1$ is a C$_1$-C$_{12}$ alkyl group which may be substituted or an aryl group which may be substituted.

The C$_1$-C$_{12}$ alkyl group may be linear, branched or cyclic. Examples of such alkyl group preferably includes methyl, ethyl, butyl, pentyl, hexyl, heptyl, octyl, nonyl, decanyl, undecanyl, dodecanyl, tridecanyl, tetradecanyl, pentadecanyl, hexadecanyl, heptadecanyl, octadecanyl, nonadecanyl, eicosanyl, cyclohexyl and benzyl.

Of the above alkyl groups, particularly preferred are alkyl groups having 4 to 12 carbon atoms and a benzyl group.

As the unsubstituted aryl group, phenyl and naphthyl are preferably used.

The above alkyl and aryl groups may mono- or multi-substituted with substituent(s) selected from the group consisting of hydroxyl, carboxyl, carbonyl, sulfonyl, sulfonium, an amino group, an ammonium group, an alkyl group, an alkoxyl group and a halogen atom.

The above amino group preferably includes NH$_2$, methylamino, dimethylamino, ethylamino and diethylamino.

The ammonium group preferably includes ammonium bases of the above amino groups.

The alkyl or alkoxyl group preferably includes linear or branched alkyl or alkoxyl group having 1 to 6 carbon atoms.

The halogen atom preferably includes fluorine, chlorine and bromine.

The organo-arsenic acid of the above formula (1) in which $R^2$ is other than hydroxyl, that is, $R^2$ is a $C_1$–$C_{12}$-alkyl group which may be substituted or an aryl group which may be substituted, refers to an arsinic acid of the formula (1)-a,

wherein $R^1$ is as defined above, and $R^{21}$ is the same group as that which defines $R^1$.

The arsinic acid of the above formula (1)-a in which $R^1$ and $R^{21}$ are the same or different and are selected from a $C_1$–$C_{12}$ alkyl group which may be substituted refers to dialkylarsinic acid.

The arsinic acid of the above formula (1)-a in which $R^1$ and $R^{21}$ are the same or different and are selected from an aryl group which may be substituted refers to diarylarsinic acid.

The arsinic acid of the above formula (1)-a preferably includes dimethylarsinic acid, dihexylarsinic acid, dibutylarsinic acid, diphenylarsinic acid, phenyl-(4-sodiumsulfonylphenyl)arsinic acid, phenyl-(4-methoxyphenyl)arsinic acid, di(4-methoxyphenyl)arsinic acid, phenyl-(4-chlorophenyl)arsinic acid, di(4-chlorophenyl)arsinic acid, phenyl-(3,5-dichlorophenyl)arsinic acid, phenyl-(4-trifluoromethyl)arsinic acid, phenyl-(4-methylphenyl)arsinic acid, phenyl-(4-dimethylaminophenyl)arsinic acid, phenyl-(4-fluorophenyl)arsinic acid, phenyl-(4-bromophenyl)arsinic acid, phenyl-(4-hydroxyphenyl)arsinic acid, benzylphenylarsinic acid, butylphenylarsinic acid and hexylphenylarsinic acid.

Of the above arsinic acids, particularly preferred are diphenylarsinic acid, phenyl-(4-methoxyphenyl)arsinic acid, phenyl-(sodiumsulfonylphenyl)arsinic acid, phenyl-(4-chlorophenyl)arsinic acid, di(4-chlorophenyl)arsinic acid, phenyl-(3,5-dichlorophenyl)arsinic acid, phenyl-(4-trifluoromethyl)arsinic acid and benzylphenylarsinic acid.

The organo-arsenic acid of the above formula (1) in which $R^2$ is hydroxyl refers to an arsonic acid of the formula (1)-b,

wherein $R^1$ is as defined in the above formula (1).

The arsonic acid of the above formula (1)-b in which $R^1$ is a $C_1$–$C_{12}$ alkyl group which may be substituted refers to an alkylarsonic acid.

Further, the arsonic acid of the above formula (1)-b in which $R^1$ is an aryl group which may be substituted refers to arylarsonic acid.

The arsonic acid of the above formula (1)-b preferably includes, for example, phenylarsonic acid, butylarsonic acid and p-methoxyarsonic acid. Of the above arsonic acids, phenylarsonic acid is particularly preferred.

The organo-arsenic acid of the above formula (1) in which $R^1$ and $R^2$ bond to each other to form a five-membered or six-membered ring together with As atoms to which these groups are bonded, preferably refers to any one of O,O'-diphenylylenearsinic acid of the formula

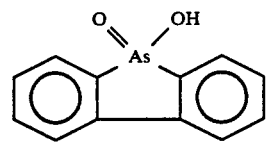

and compounds of the formula

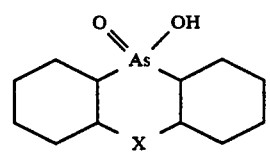

wherein X is $CH_2$, NH or O, such as arsacridinic acid (X=$CH_2$), phenarsazinic acid (X=NH) and phenoxyphenylarsinic acid (X=O).

The process of the present invention is carried out by allowing a carbonyl compound and hydrogen peroxide to react in the presence of the above organo-arsenic acid as a catalyst.

In the above reaction, the organo-arsenic acid may be used as a catalyst prepared by allowing an organic or inorganic carrier to carry it thereon.

The catalyst can be selected depending upon an intended carboxylated compound in view of not only a reaction yield but also demands in the process such as separation from the reaction liquid and the recycling.

The amount of the catalyst for use per kg of the reaction liquid is preferably not more than 100 g, more preferably 0.1 g to 75 g, particularly preferably 0.5 to 50 g. The catalyst can be introduced into the reaction system by a variety of known methods. For example, the catalyst may be a pure crystal or may be used by dissolving it in one component of the reaction liquid.

The carbonyl compound used in the present invention includes ketones and aldehydes having 4 to 20 carbon atoms. Preferred as a ketone are, for example, noncyclic ketones such as methyl ethyl ketone, diethyl ketone and acetophenone; and cyclic ketones such as cyclopentanone, cyclohexanone, methylcyclohexanone, cyclohexenone, cyclooctanone, isophorone, camphor, fluorenone and naphthoquinone. Preferred as an aldehyde are, for example, vanillin, benzaldehyde, tolualdehyde and 2,6-dimethylbenzaldehyde.

According to the present invention, esters can be produced from ketones as starting materials, and esters or carboxylic acids can be produced from aldehydes as starting materials.

In the present invention, hydrogen peroxide may be used as an aqueous solution or as a solution of it in an organic solvent.

The selection between the above solutions can be determined on the basis of demands in the process. In general, an aqueous solution of hydrogen peroxide is used. The selection of the concentration of a hydrogen peroxide solution for use can be made in a wide range. When an aqueous solution of hydrogen peroxide is used, hydrogen peroxide concentration is used generally in a concentration of not less than 10% by weight. In view of operability and safety, however, the concentration of more than 90% by weight should be avoided.

The concentration is preferably in the range of from 20 to 80% by weight.

In the present invention, the selection of the amount ratio of the hydrogen peroxide to the carbonyl compound in the reaction medium can be made in a wide range depending upon the reaction rate and a solvent used. In general, the amount ratio is preferably in such a range that the molar amount of the hydrogen peroxide is not more than 1.5 times the molar amount of he carbonyl compound.

In the present invention, there may be used a solvent in addition to the carbonyl compound, the hydrogen peroxide and the catalyst. A solvent which is inert under reaction conditions is generally used as such. The solvent preferably includes ethers, alcohols, halogenated hydrocarbons, hydrocarbons, carboxylate esters and phosphate esters.

The solvent which is preferably usable is selected from ethers having 4 to 14 carbon atoms such as diethyl ether, diphenyl ether, diglyme and tetrahydrofuran; mono- or polyhydric primary, secondary or tertiary alcohols having 1 to 12 carbon atoms such as methanol, ethanol, tert-butanol, cyclohexanol, ethylene glycol and 1,4-butanediol; aliphatic or aromatic, halogenated hydrocarbons having 2 to 10 carbon atoms, preferably chlorinated or fluorinated hydrocarbons; aliphatic or aromatic hydrocarbons having 6 to 20 carbon atoms such as n-hexane, cyclohexane, decane, benzene, toluene, xylene and mesitylene; aliphatic or alicyclic carboxylic acid esters having 2 to 6 carbon atoms such as methyl acetate, phenyl acetate, methyl propionate, methyl caproate and $\epsilon$-caprolactone; and phosphate esters having 3 to 21 carbon atoms such as trimethyl phosphate, triethyl phosphate and triphenyl phosphate. Besides the above inert solvents, organic acids including carboxylic acids such as acetic acid, propionic acid and caproic acid may be used as the solvent. When an organic acid is used as a solvent, part of the organic acid is sometimes converted to peroxide to promote the reaction and inhibit the formation of by-products.

The amount of the solvent can be determined in a wide range and is generally in a range of 0 to 90% by weight. When a cyclic ketone is a starting material, no solvent is used in most cases, since the cyclic ketone works as a solvent. The reaction temperature is normally not more than 150° C., generally between 50° C. and 130° C. In particular, when the reaction temperature is between 70° C. and 120° C., a favorable result can be obtained. Although differing depending upon whether or not water is removed from the reaction system, the reaction pressure is set in the range from $1 \times 10^3$ Pa to $3 \times 10^5$ Pa.

The presence of a large amount of water in the reaction system not only causes a decrease in the reaction rate and an increase in the formation of peroxides, but also tends to decrease the yield of an ester due to hydrolysis of the formed ester in the oxidation of ketones. In the reaction system, it is preferred to maintain the water concentration at a level equal to or below the level at which the reaction medium and water form a uniform phase. The water concentration in the reaction system varies depending upon temperatures. However, for example, when a uniform phase is formed of the reaction medium using cyclohexanone as a starting material, the water concentration at room temperature is preferably not more than 8% by weight. In general, the water concentration in the system is preferably not more than 2% by weight, more preferably not more than 0.5% by weight, particularly preferably not more than 0.2% by weight. It is preferred to remove water from the reaction system by azeotropy of either the reaction solvent or the material and water. When the azeotropy temperature is higher than the reaction temperature, water may be removed by a method in which the reaction is carried out under reduced pressure, or an inert gas is blown into the reaction system to carry vapor.

In addition, there may be employed a method in which water is physicochemically or chemically removed. For example, water in the reaction system may be converted to crystal water of inorganic salt, or water may be trapped in a cavity of a molecular sieve. Further, water in the system may be removed by allowing it to react with acid anhydride. In this case, a compound which has worked as a dehydrating agent may be recycled, for example, after drying or dehydrating it.

The reaction in the present invention is usually carried out until hydrogen peroxide is substantially used up. The present invention may be carried out with any one of a single reactor and a continuous multi-reactor apparatus, and it may be carried out by any one of a continuous method and a non-continuous method. Further, a tube-type reactor may be employed.

The present invention uses the above-specified organo-arsenic acid as a catalyst, whereby a carboxylated compound can be very effectively produced from a carbonyl compound and hydrogen peroxide at a high reaction rate and at high yields.

The present invention will be described further in detail by reference to Examples, which are presented for description and are not intended to limit the present invention.

EXAMPLE 1

A reaction flask equipped with a stirrer, a condenser and a water separator was charged with 88 g of cyclohexanone and 1 g of dimethylarsinic acid, and while the mixture was stirred, the temperature in the flask was elevated up to 90° C. Then, 18.5 g of 35% hydrogen peroxide water was introduced over 3 hours. During this procedure, a nitrogen gas was blown into the flask and water was removed by azeotropic distillation of it with cyclohexanone.

After the reaction finished, the reaction liquid was analyzed by high-speed liquid chromatography to show the formation of 16.1 g of $\epsilon$-caprolactone. The yield on the basis of the hydrogen peroxide was 74%.

EXAMPLE 2

The same flask as that used in Example 1 was charged with 88 g of cyclohexanone and 1 g of dimethylarsinic acid, and while the mixture was stirred, the temperature in the flask was elevated up to 120° C. Then, 10.8 g of 60% hydrogen peroxide water was introduced over 1 hour. After the reaction finished, the reaction liquid was analyzed by high-speed liquid chromatography to show the formation of 15.0 g of $\epsilon$-caprolactone. The yield on the basis of the hydrogen peroxide was 69%.

EXAMPLE 3

The reaction in Example 1 was repeated except that 1 g of the dimethylarsinic acid was replaced with 0.5 g of diphenylarsinic acid and that 10.8 g of 60% hydrogen peroxide water was introduced over 3 hours at a reaction temperature of 90° C. After the reaction finished, the reaction liquid was analyzed to show the formation of 19.8 g of ε-caprolactone. The yield on the basis of the hydrogen peroxide was 91%.

EXAMPLE 4

The reaction in Example 1 was repeated except that 1 g of the dimethylarsinic acid was replaced with 1 g of dihexylarsinic acid and that 10.8 g of 60% hydrogen peroxide water was introduced over 1 hour at a reaction temperature of 110° C. After the reaction finished, the reaction liquid was analyzed to show the formation of 18.6 g of ε-caprolactone. The yield on the basis of the hydrogen peroxide was 86%.

EXAMPLE 5

The reaction in Example 1 was repeated except that 1 g of the dimethylarsinic acid was replaced with 1 g of dibutylarsinic acid and that 10.8 g of 60% hydrogen peroxide water was introduced over 1.5 hours at a reaction temperature of 100° C. After the reaction finished, the reaction liquid was analyzed to show the formation of 18.0 g of ε-caprolactone. The yield on the basis of the hydrogen peroxide was 83%.

EXAMPLE 6

The reaction in Example 1 was repeated except that the same flask as that used in Example 1 was charged with 60 g of cyclohexanone and 28 g of acetic acid and that 3.6 g of 60% hydrogen peroxide water was introduced over 1 hour. After the reaction finished, the reaction liquid was analyzed to show the formation of 5.6 g of ε-caprolactone. The yield on the basis of the hydrogen peroxide was 77%.

EXAMPLE 7

The reaction in Example 3 was repeated except that 88 g of the cyclohexanone was replaced with 88 g of benzaldehyde. After the reaction finished, the reaction liquid was analyzed by high-speed liquid chromatography to show the formation of 71%, based on the hydrogen peroxide, of benzoic acid and phenol.

EXAMPLE 8

The reaction in Example 3 was repeated except that 0.5 g of the diphenylarsinic acid was replaced with 0.5 g of phenyl-(4-chlorophenyl)arsinic acid and that 21.6 g of 60% hydrogen peroxide water was introduced over 2 hours at a reaction temperature of 120° C. After the reaction finished, the reaction liquid was analyzed to show the formation of 39.4 g of ε-caprolactone. The yield on the basis of the hydrogen peroxide was 90.6%. The water content in the reaction system was 0.06% by weight.

EXAMPLE 9

The reaction in Example 3 was repeated except that 0.5 g of the diphenylarsinic acid was replaced with 0.5 g of phenyl-(4-sodiumsulfonylphenyl)arsinic acid and that 5.4 g of 60% hydrogen peroxide water was introduced over 1 hour at a reaction temperature of 110° C. After the reaction finished, the reaction liquid was analyzed to show the formation of 9.4 g of ε-caprolactone. The yield on the basis of the hydrogen peroxide was 87%. The water content in the reaction system was 0.13% by weight. The reaction liquid was subjected to extraction with water to show that at least 99% of the catalyst was present in a water phase.

EXAMPLE 10

The reaction in Example 3 was repeated except that 88 g of the cyclohexanone was replaced with 88 g of methylcyclohexanone and that 10.8 g of 60% hydrogen peroxide water was introduced over 2 hours at a reaction temperature of 110° C. After the reaction finished, the reaction liquid was analyzed to show the formation of 17.3 g of methyl caprolactone. The yield on the basis of the hydrogen peroxide was 81%. The water content in the reaction system was 0.09% by weight.

EXAMPLE 11

The reaction in Example 3 was repeated except that 0.5 g of the diphenylarsinic acid was replaced with 0.5 g of di(4-methoxyphenyl)arsinic acid and that 16.2 g of 60% hydrogen peroxide water was introduced over 3 hours. After the reaction finished, the reaction liquid was analyzed to show the formation of 29.2 g of ε-caprolactone. The yield on the basis of the hydrogen peroxide was 89.5%. The water content in the reaction system was 0.08% by weight.

EXAMPLE 12

The reaction in Example 3 was repeated except that the reaction temperature was changed to 120° C. and that 16.2 g of 60% hydrogen peroxide water was introduced over 2 hours. After the reaction finished, the reaction liquid was analyzed to show the formation of 29.0 g of ε-caprolactone. The yield on the basis of the hydrogen peroxide was 88.9%. The water content in the reaction system was 0.07% by weight.

EXAMPLE 13

The reaction in Example 3 was repeated except that 0.5 g of the diphenylarsinic acid was replaced with 0.5 g of di(4-chlorophenyl)arsinic acid and that 10.8 g of 60% hydrogen peroxide water was introduced over 1 hour at a reaction temperature of 110° C. After the reaction finished, the reaction liquid was analyzed to show the formation of 20.7 g of ε-caprolactone. The yield on the basis of the hydrogen peroxide was 95.5%. The water content in the reaction system was 0.05% by weight.

EXAMPLE 14

The reaction in Example 3 was repeated except that 0.5 g of the diphenylarsinic acid was replaced with 0.5 g of phenyl-(3,5-dichlorophenyl)arsinic acid and that 5.4 g of 60% hydrogen peroxide water was introduced over 0.5 hour at a reaction temperature of 110° C. After the reaction finished, the reaction liquid was analyzed to show the formation of 10.4 g of ε-caprolactone. The yield on the basis of the hydrogen peroxide was 95.9%. The water content in the reaction system was 0.05% by weight.

EXAMPLE 15

The reaction in Example 3 was repeated except that 0.5 g of the diphenylarsinic acid was replaced with 0.5 g of phenyl-(4-trifluoromethylphenyl)arsinic acid and that 10.8 g of 60% hydrogen peroxide water was introduced over 1 hour at a reaction temperature of 120° C. After the reaction finished, the reaction liquid was analyzed to show the formation of 20.3 g of ε-caprolactone. The yield on the basis of the hydrogen peroxide was 93.6%. The water content in the reaction system was 0.05% by weight.

EXAMPLE 16

A reaction flask was charged with 88 g of cyclohexanone and 1 g of phenylarsonic acid, and while the mixture was stirred, the temperature inside the flask was elevated up to 120° C. Then, 10.8 g of 60% hydrogen peroxide water was introduced over 2 hours. During this procedure, a nitrogen gas was blown into the system to azeotropically remove water. After the reaction finished, the reaction liquid was analyzed by high-speed liquid chromatography to show the formation of 18.4 g of ε-caprolactone. The yield on the basis of the hydrogen peroxide was 85%. The water content in the reaction system was 0.08% by weight.

EXAMPLE 17

The reaction in Example 16 was repeated except that 1 g of the phenylarsonic acid was replaced with 1 g of butylarsonic acid and that 10.8 g of 60% hydrogen peroxide water was introduced over 2 hours at a reaction temperature of 120° C. After the reaction finished, the reaction liquid was analyzed to show the formation of 15.4 g of ε-caprolactone. The yield on the basis of the hydrogen peroxide was 71%. The water content in the reaction system was 0.2% by weight.

EXAMPLE 18

The reaction in Example 16 was repeated except that 1 g of the phenylarsonic acid was replaced with 1 g of p-methoxyphenylarsonic acid and that 10.8 g of 60% hydrogen peroxide water was introduced over 1.5 hours at a reaction temperature of 120° C. After the reaction finished, the reaction liquid was analyzed to show the formation of 18.0 g of ε-caprolactone. The yield on the basis of the hydrogen peroxide was 83%. The water content in the reaction system was 0.06% by weight.

EXAMPLE 19

The reaction in Example 3 was repeated except that 0.5 g of the diphenylarsinic acid was replaced with 0.5 g of 0,0'-diphenylylenearsinic acid and that the reaction temperature was changed to 110° C. After the reaction finished, the reaction liquid was analyzed to show the formation of 9.5 g of ε-caprolactone. The yield on the basis of the hydrogen peroxide was 44%. The water content in the reaction system was 0.08% by weight.

What is claimed is:

1. A process for producing a carboxylated compound, which comprises reacting a cyclic ketone with hydrogen peroxide in the presence of an organo-arsinic acid of the formula (1),

to form a reaction system, the reaction system containing not more than 2% by weight of water during the reaction, wherein each of $R^1$ and $R^2$ is, independently, a $C_{1-12}$ alkyl group which may be substituted or an aryl group which may be substituted, or alternatively, $R^1$ and $R^2$ may bond to each other to form a five-membered or six-membered ring together with As atoms to which these groups are bonded, and the substituent(s) substituted on the above groups is/are selected from hydroxyl, carboxyl, carbonyl, sulfonyl, sulfonium, amino, ammonium, alkyl, alkoxy and halogen, to thereby form the corresponding carboxylated compound which is a lactone.

2. The process of claim 1, wherein the arsinic acid is a dialkylarsinic acid of the formula (1) in which each of $R^1$ and $R^2$ is the same as, or different from, the other and is a $C_1$–$C_{12}$ alkyl group which may be substituted.

3. The process of claim 1, wherein the arsinic acid is a diarylarsinic acid of the formula (1) in which each of $R^1$ and $R^2$ is the same as, or different from, the other and is an aryl group which may be substituted.

4. The process of claim 3, wherein the diarylarsinic acid is diphenylarsinic acid which may be substituted.

5. The process of claim 1, wherein the cyclic ketone is cyclohexanone and the corresponding carboxylated compound formed is ε-caprolactone.

6. The process of claim 1, wherein the water concentration in the reaction system is maintained at not more than 0.5% by weight.

7. The process of claim 1, wherein the water concentration in the reaction system is maintained at not more than 0.2% by weight.

8. The process of claim 1, wherein the water is removed by azeotropy of either the reaction solvent or the material and water.

9. The process of claim 1, wherein the water is removed by carrying out the reaction under reduced pressure.

10. The process of claim 1, wherein the water is removed by blowing inert gas into the reaction system.

11. The process of claim 1, wherein the concentration of hydrogen peroxide is 10 to 80% by weight.

12. The process of claim 1, wherein the concentration of hydrogen peroxide is 20 to 80% by weight.

* * * * *